United States Patent [19]

Liburdy

[11] Patent Number: 4,472,506

[45] Date of Patent: Sep. 18, 1984

[54] METHOD FOR DETERMINING CELL MEMBRANE DIELECTRIC BREAKDOWN

[76] Inventor: Robert P. Liburdy, 1245 Park Ave., Apt. 16A, New York, N.Y. 10128

[21] Appl. No.: 425,360

[22] Filed: Sep. 28, 1982

Related U.S. Application Data

[62] Division of Ser. No. 224,781, Jan. 13, 1981, Pat. No. 4,368,423.

[51] Int. Cl.³ .......................................... G01N 27/04
[52] U.S. Cl. ..................................... 436/63; 204/1 T; 324/65 R; 436/149
[58] Field of Search ................. 436/63, 150, 151, 149; 204/403, 1 T, 195 B; 324/71 CP, 71 R, 65 R

[56] References Cited

U.S. PATENT DOCUMENTS

| | | | |
|---|---|---|---|
| 2,656,508 | 10/1953 | Coulter | 324/71 CP |
| 3,772,591 | 11/1973 | Louder et al. | 324/30 R |
| 3,810,010 | 5/1974 | Thom | 324/71 CP |
| 3,890,569 | 6/1975 | Hogg | 324/71 CP |
| 3,999,944 | 12/1976 | Grosser et al. | |
| 4,011,044 | 3/1977 | Uzgiris | |
| 4,043,757 | 8/1977 | Wagstaff | |
| 4,055,799 | 10/1977 | Coster et al. | 204/195 B X |
| 4,081,241 | 3/1978 | Porzsolt et al. | |
| 4,103,229 | 7/1978 | Gear | 324/71 CP |
| 4,343,782 | 8/1982 | Shapiro | 436/63 X |

OTHER PUBLICATIONS

Thorn et al., "A Simplified Cr-Release Assay for Killer Cells," Journal of Imm. Methods, vol. 4, 1974, pp. 301-315.
Brunner et al., "In Vitro Methods in Cell-Mediated and Tumor Immunity," Edited by Bloom et al., Pub. Academic Press, NY, San Francisco, London, 1976, pp. 423-428.
Petitou et al., "Decreased Microviscosity-Mechanisms," Proc. Natl. Acad. Sci. USA, vol. 75, No. 5, May 1978, pp. 2306-2310.
Kapitulnik et al., "Fluidity of the Rat Liver Microsomal Membrane: Increase at Birth", Science, vol. 206, No. 16, 1979, pp. 843-844.
Shimitzky et al., "Effective Tumor-Microviscosity," Proc. Nat. Acad. Sci. USA, vol. 76, No. 10, Oct. 1979, pp. 5313-5316.
Martz, "Contemporary Topics in Immunobiology", vol. 7, Edited by Stutman, Pub. Plenum Press, NY and London, 1977, Chap. 9, pp. 301-361.
Harrington, "Differing Time Courses of Spleen Leukocyte MIF Synthesis and Cytotoxicity During Rejection of a Murine Lymphoma Allograft," Cellular Immunology, vol. 24, pp. 195-201, 1976.
Crowley, "Electrical Breakdown of Bimolecular Lipid Membranes as an Electromechanical Instability," Biophysical Journal, vol. 13, 1973, pp. 711-725.
Hoffman et al., "Flow System Measurement of Cell Impedance Properties," The Journal of Histochemistry and Cytochemistry, vol. 27, No. 1, 1979, pp. 234-240.
Van Blitterswijk et al., "Quantitation of Virus-Induced (MLR) and Normal-Leukemia Cells", Cancer Research, 35, Oct. 1975, pp. 2743-2751.

*Primary Examiner*—Arnold Turk
*Attorney, Agent, or Firm*—Donald J. Singer; Jacob N. Erlich

[57] ABSTRACT

A method and apparatus which enables cell membrane dielectric breakdown to be determined. This determination is essential for the rapid inexpensive, reliable, in vitro quantification of lymphocyte tumor-cell cytotoxicity, lymphocyte membrane fluidity and the analysis of abnormal or tumor cells. The apparatus incorporates therein a cell dispenser used in conjunction with a DC electric field exposure tube. Electronic circuitry and its associated components process, acquire and store cell voltage signals as the cells are drawn through the electric field exposure tube. The procedure involves quantifying the breakdown voltage required to electrically collapse the cell membrane. The electrical collapse is termed a dielectric breakdown and is characterized by a reversible drop in the cell's resistivity.

2 Claims, 9 Drawing Figures

METHOD FOR DETERMINING CELL MEMBRANE DIELECTRIC BREAKDOWN

STATEMENT OF GOVERNMENT INTEREST

The invention described herein may be manufactured and used by or for the Government for governmental purposes without the payment of any royalty thereon.

This is a division of application Ser. No. 224,781, filed Jan. 13, 1981, now U.S. Pat. No. 4,368,423.

BACKGROUND OF THE INVENTION

This invention relates generally to the field of medical diagnostics, and, more particularly, to a method for determining cell membrane dielectric breakdown and lymphocyte cell membrane fluidity in order to establish lymphocyte tumor-cell cytotoxicity as well as the presence of actual tumor-cells.

The lymphatic system of vessels in the vertebrate body begins in a network of exceedingly thin-walled capillaries in almost all the organs and tissues except the brain and bones. This network is drained by larger channels, mostly coursing along the veins and eventually joining to form a large vessel, the thoracic duct, which runs beside the spinal column to enter the left subclavian vein at the base of the neck. The lymph fluid originates in the tissue spaces by filtration from the blood capillaries, while in the lymphatic capillaries it is clear and watery. However, at intervals along the larger lymphatic vessels, the lymph passes through spongelike lymph nodes, where it receives great numbers of cells, the lymphocytes, and becomes turbid.

Lymphocytes are of different sizes; small, medium, and large. The range in size of these three kinds, however, varies with different classes and even species of animals. The large lymphocyte resembles very closely the stem cell of blood-forming tissue, the hemocytoblast. In fact, lymphoid tissue itself bears a considerable resemblance to hematopoietic tissue, and in lower vertebrates it is not always possible to distinguish one from the other.

In general, the lymphocyte is responsible for in vivo identification and removal of foreign, non-self material. Such material can be in the form of antigenic particulates, bacterial and virial bodies, and their associated soluble materials. The lymphocyte thus acts as a surveillance network primed to recognize and clear from the body's blood stream and tissues all potentially harmful irritants; it is the body's main line of defense and it is crucial to the maintenance of an organism's state of health.

There are several different types of lymphocytes required to accomplish the task of defending an organism against infection and disease. The following cell-types have been recognized based on their biological activity in vivo: $T_d$ cells are responsible for delayed-hypersensitivity reactions; $T_s$ cells are responsible for regulating cell-mediated immune reactions through suppression of other lymphocyte activities; $T_h$ cells are helper cells involved in antibody production; B lymphocytes are antibody producing cells; and $T_c$ lymphocytes are responsible for cell-mediated cytotoxicity reactions.

The $T_c$ lymphocyte functions as a killer cell towards invading tumor cells, bacteria, and virions, and its nomenclature, cytotoxic lymphocyte, derives from activity. These cells are crucial to thwarting foreign cell proliferation in vivo, and controlling and enhancing or potentiating their activity is a goal of chemical investigators interested in altering the balance of immune reactions in favor of the patient combating disease.

Accordingly, it is of major importance to determine whether an individual suspected of carrying a disease process, like a neoplastic or cancer cell, has functionally active $T_c$ lymphocytes. This information will reflect the patient's $T_c$ lymphocyte capacity to destroy the invading cell population.

A prior technique utilized to assay for cytotoxic activity of lymphocytes is set forth in, for example, the publication by John T. Harrington, Jr., entitled "Differing Time Courses of Spleen Leukocyte MIF Synthesis and Cytotoxicity During Rejection of a Murine Lymphoma Allograft," *Cellular Immunology,* Vol. 24, pgs 195–201, 1976 and described by Eric Martz, in the publication *Contemporary Topics in Immunobiology,* Vol. 7, pg 301, 1977. Such a technique is laborious, lengthy, expensive, and potentially hazardous. For example, the past procedure involves culturing lymphocytes in the presence of radioactively labeled tumor cells for approximately four hours under conditions of controlled temperature and humidity, and then measuring the cummulative release of radioactive radioisotope from the tumor cell as they are lysed or ruptured by the lymphocytes. This in vitro measurement of tumor cell death is believed to be correlated to in vivo cytotoxic activity of $T_c$ cells.

The actual events that occur during the process of cytotoxicity are complicated and not well understood, but they presumably involve permeability changes in the tumor cell induced by cell contact with $T_c$ lymphocytes; this contact is essential and called the "lethal hit". The release of radioactive radioisotope from the tumor cell in this assay is believed to represent tumor cell death.

As stated above the prior technique is extremely lengthy in that tumor and lymphocytes must be prepared and cultured in an incubator for four hours. The assay involves the use of radioactive isotopes and requires strict safety and handling precautions. In addition, the incubation chamber, gas tanks, the radioactive isotope, and the well-geiger counter for quantitating radioactivity utilized with the past procedure are extremely expensive.

It is therefore essential in the field of medical diagnostics and more particularly in the field which encompasses the management of tumor-associated disease processes to obtain a reliable, fast, inexpensive in vitro alternative to the past technique in the quantification of lymphocytes tumor-cell cytotoxicity and lymphocyte membrane fluidity.

SUMMARY OF THE INVENTION

The instant invention overcomes the problems encountered in the past by providing a method for determining cell membrane dielectric breakdown and thereby is capable of performing a reliable, fast, inexpensive, in vitro quantification of lymphocyte tumor-cell cytotoxicity, lymphocyte membrane fluidity and the establishment of the presence of abnormal or tumor cells.

Essentially the test procedure of this invention involves quantifying the breakdown voltage required to electrically collapse the cell membrane. The electrical collapse is termed a dielectric breakdown and is characterized by a reversible change in the cell's resistivity. In the case of the lymphocyte, the voltage at which its membrane undergoes dielectric breakdown (the breakdown voltage) is directly correlated to cytotoxic function, as is clearly demonstrated hereinbelow.

The apparatus for determining the cell membrane dielectric breakdown is made up of a receptacle for containing an electrolyte solution, a DC electric field exposure tube having a minute port therein, electronic circuitry and its associated components capable of processing, acquiring and storing lymphocyte voltage signals and a lymphocyte storage tube which directs through a nozzle a stream of lymphocytes or other cells to be tested.

The cells are drawn through the port within the electric field exposure tube by means of a vacuum attached thereto. A DC electric field is established across the port so that the cells are exposed to an intense electric field gradient as they transverse the port. This action causes a voltage transient in the electric field. The voltage pulses are monitored by the electronic components which contain therein an oscilloscope and frequency counter in order to insure that proper cell exposure and flow rate are maintained. The voltage pulses are stored in a multi-channel pulse-height analyzer and a frequency histogram is constructed based on peak-pulse height. The magnitude of the average voltage pulse height is associated with each different applied voltage is revealed in the histogram. This average voltage pulse height can be plotted against the applied voltage to determine or obtain a breakdown profile of the cells.

Live lymphocytes display a distinct breakdown in their linear profile. The voltage at which this occurs is the breakdown point voltage and it indicates that the lymphocyte cell membrane has undergone dielectric collapse and cell electrical resistivity has been markedly reduced giving rise to the characteristic breakdown profile. This cell electrical resistivity is directly related to the fluidity of the cell membrane. Lymphocyte cells which are cytotoxic possess decreased cell membrane fluidity and therefore establish varying characteristic cell-membrane breakdown profiles.

In this manner, the instant invention provides a method which can reliably and quickly determine cell membrane dielectric breakdown and therefore, more particularly, establish lymphocyte tumor-cell cytotoxicity as well as directly establish the presence of abnormal cells such as tumor cells.

It is therefore an object of this invention to provide a method for determining cell membrane dielectric breakdown.

It is a further object of this invention to provide a method which are capable of reliably, quickly and and inexpensively, in vitro, determining cell membrane dielectric breakdown.

It is still a further object of this invention to provide a method which is capable of quantifying lymphocyte tumor-cell cytotoxicity, lymphocyte membrane fluidity and the presence of abnormal or tumor-cells.

It is still a further object of this invention to provide a method for determining cell membrane dielectric breakdown which is economical, and utilizes conventional, currently available components that lend themselves to standard mass producing manufacturing techniques.

For a better understanding of the present invention together with other and further objects thereof, reference is made to the following description taken in conjunction with the accompanying drawing and its scope will be pointed out in the appended claims.

DETAILED DESCRIPTION OF THE DRAWING

DETAILED DESCRIPTION OF THE PREFERRED EMBODIMENT AND METHOD

Figure 1:
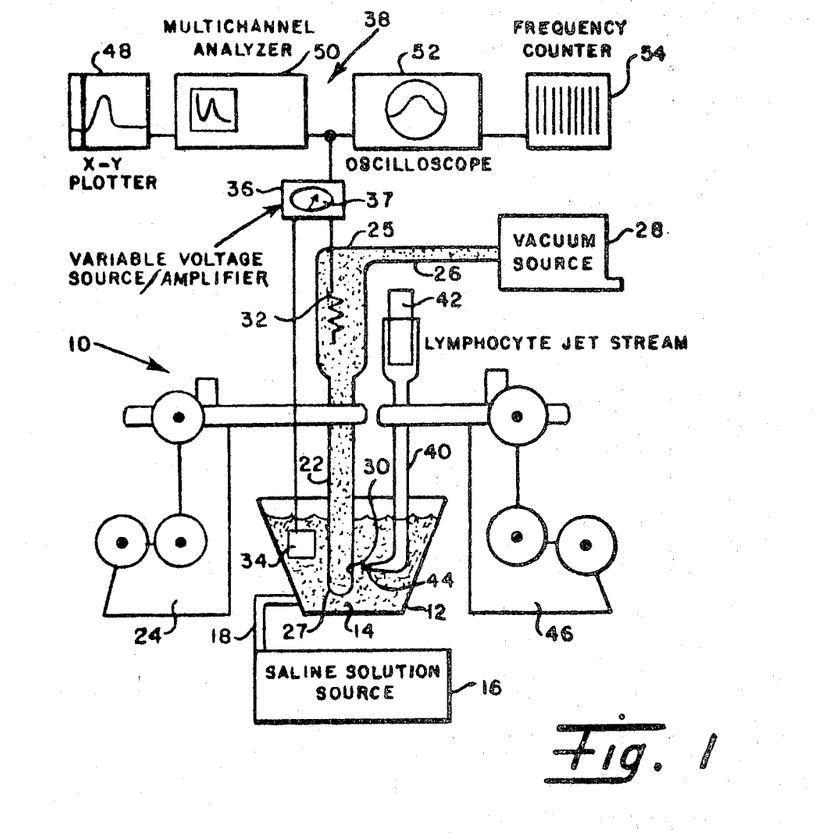
FIG. 1 is a schematic representation of the apparatus for determining cell membrane dielectric breakdown.

Reference is now made to FIG. 1 of the drawing which best illustrates the apparatus 10 for determining cell membrane dielectric breakdown. Apparatus 10 is made up of any suitable receptacle 12 which contains therein an electrolyte solution in the form, of example, a conventional saline solution 14. The saline solution 14 is continuously fed into receptacle 12 by any suitable saline source 16 which may include a pump (not shown), if necessary, for feeding the saline solution 14 through a tube or line 18 operably connected to an opening (not shown) within a sidewall of receptable 12. The saline solution 14 exits receptacle 12 by means of an electric field exposure tube 22 in a manner to be described in detail hereinbelow.

Electric field exposure tube 22 is disposed within receptacle 12 by being either fixedly or adjustably secured in place by any suitable mounting member 24. Electric field exposure tube 22 is made of non-conductive material such as glass and may in fact take on the shape of a conventional test tube configuration, if desired. One end 25 of tube 22 has formed therein an exit line 26 which is operably connected to any suitable vacuum source 28 while the other end 27 of tube 22 is located within the saline solution 14 within receptacle 12. This other end 27 has formed adjacent thereto an extremely small port 30 (illustrated in enlarged proportion). Port 30 enables the saline soultion 14 to be drawn through the electric field exposure tube 22 by the vacuum source 28. In addition, port 30 is preferably approximately 100 microns in size. More specifically, however, port 30 is approximately 10 times the diameter of a cell which undergoes examination by the apparatus 10.

A DC electric field is established across port 30 through a first electrode 32 located within the upper portion of tube 22 and a second electrode 34 situated within the saline solution 14 in receptacle 12. Electrodes 32 and 34 are electrically connected to any suitable conventional variable voltage source/amplifier 36. The voltage source/amplifier 36 also incorporates therein a digital voltmeter 37 which reads the voltage across port 30.

Also located within the saline solution 14 in receptacle 12 is a non-conductive tube-like storage container 40, having a plunger 42 situated within one end thereof and a nozzle 44 formed at the other end thereof. Container 40 contains therein the appropriate cells to be examined by the apparatus 10. The tube-like container 40 is held in adjustable relationship with port 30 of the electric exposure tube 22 within the saline solution 14 by means of any suitable adjustable mount 46 of the type utilized to mount electric field exposure tube 22 in place. The adjustability feature on mount 46 (or at least on one of the mounts 24 or 26) is essential in that it enables nozzle 44 of container 40 to be positioned proximate port 30 of exposure tube 22.

Consequently, by the application of a vacuum through exposure tube 22 not only is saline solution 14 drawn through tube 22 but also drawn therethrough are the cells to be examined. Optimum results can be obtained with the apparatus and method of this invention by controlling the vacuum source 28 in accordance with a frequency count (described in detail hereinbelow) so that approximately 2000 cells per second flow from nozzle 44 through port 30. As the cells move through port 30 they act as a resistance and a voltage increase or spike will occur. The simplified electric circuit 45 shown in FIG. 2 of the drawing is an electrical analog representation of the dielectric breakdown apparatus 10. The simplified circuit 45 is made up of voltage source 36, digital voltmeter 37, a multichannel analyzer 50, as well as a resistor R representative of the total network resistance, a capacitor C representative of the total network capacitance, and a diode D representative of the one way direction of the current within the network.

Still referring to FIG. 1 of the drawing, the electronic components 38 associated with apparatus 10 are shown. The electronic components 38 are made up of a conventional X-Y plotter 48, a conventional multi-channel analyzer 50, as for example, an Ortec 4100 MCA, referred to above with respect to circuit 45, a conventional oscilloscope 52 and a conventional frequency counter 54 which is utilized to count the number of pulses (that is the number of cells drawn through port 30).

Figure 2:
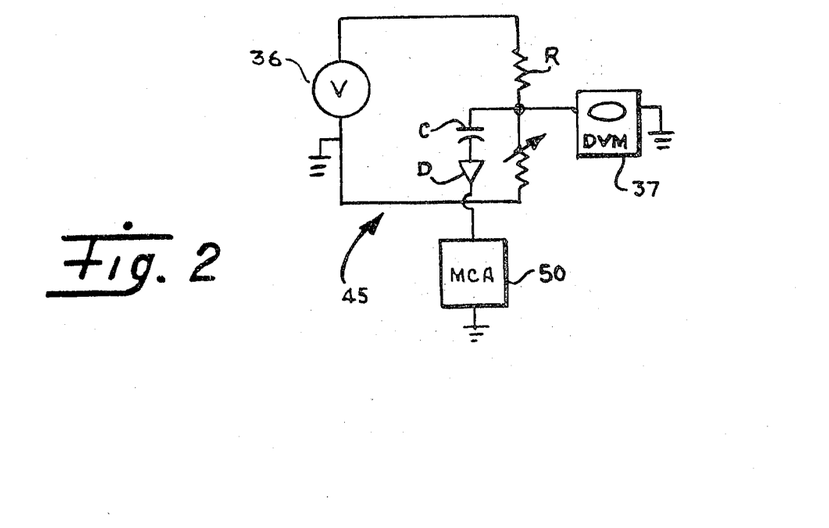
FIG. 2 is a schematic electrical analog representation of the dielectric breakdown apparatus.

More specifically, and still referring to FIGS. 1 and 2 of the drawing, an essential feature of the apparatus 10 is port 30 through which the lymphocyte cell moves and becomes exposed to a controlled, but variable, static electric field. Port 30 can be viewed as a variable resistor whose resistance increases when a cell passes into and traverses port 30. A constant, but variable voltage is applied to port 30, so apparatus 10 can be modeled as a simple voltage divider (illustrated in FIG. 2). As a cell traverses port 30 a transient increase in resistance leads to a voltage spike that is amplified and stored. The amplification is accomplished by the simple amplifier circuit 55 shown in FIG. 3 of the drawing.

Figure 3:
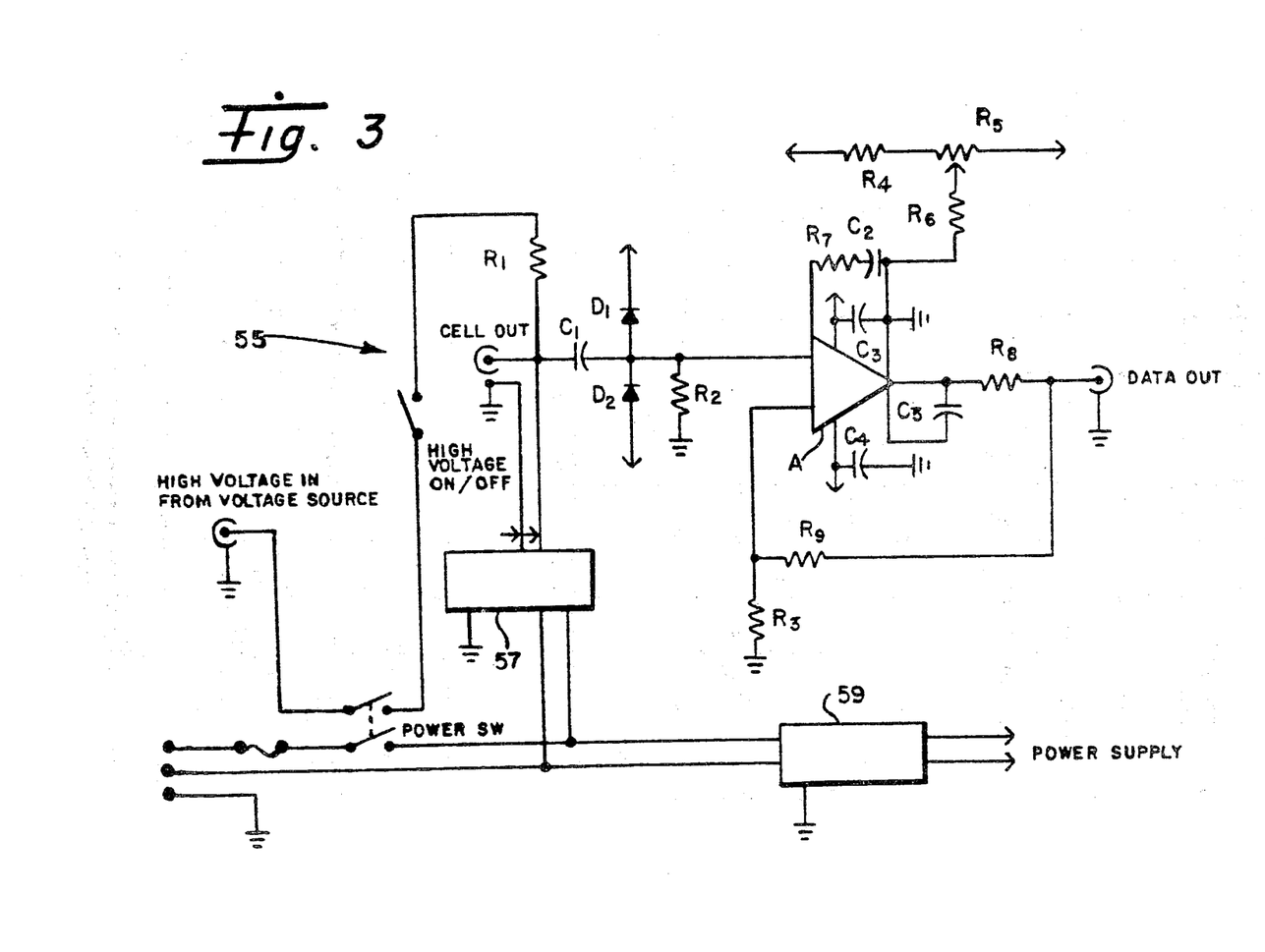
FIG. 3 is a schematic representation of the amplifier circuitry of the dielectric breakdown apparatus.

The amplifier circuit 55 is made up of a conventional amplifier A, a plurality of conventional resistors $R_1$–$R_8$, capacitors $C_1$–$C_5$, diodes $D_1$ and $D_2$ a millivolt reference voltage provided by, for example, a standard DC battery 57 and a standard 60 cycle noise filter 59. The transient voltage signals arrive at the designation "cell out", are amplified several fold and are outputted at the designation "data out". The amplified signal can be stored and sorted for pulse height on multichannel analyzer 50 as shown in FIG. 1. Although specific amplifier circuitry is illustrated in FIG. 3 of the drawing any other suitable circuitry which can accomplish the function of the amplifier circuit 55 can be utilized with this invention.

Figure 4A:
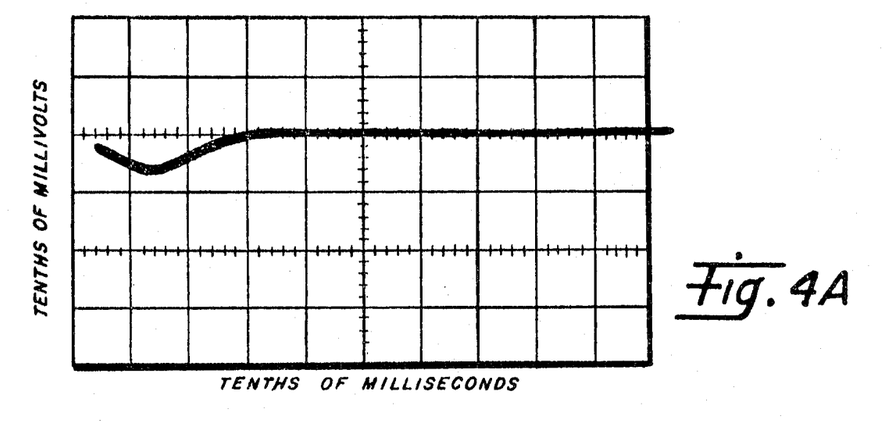
FIGS. 4A, 4B and 4C are graphic representations of typical voltage pulses obtainable with the dielectric breakdown apparatus of this invention.
Figure 4B:
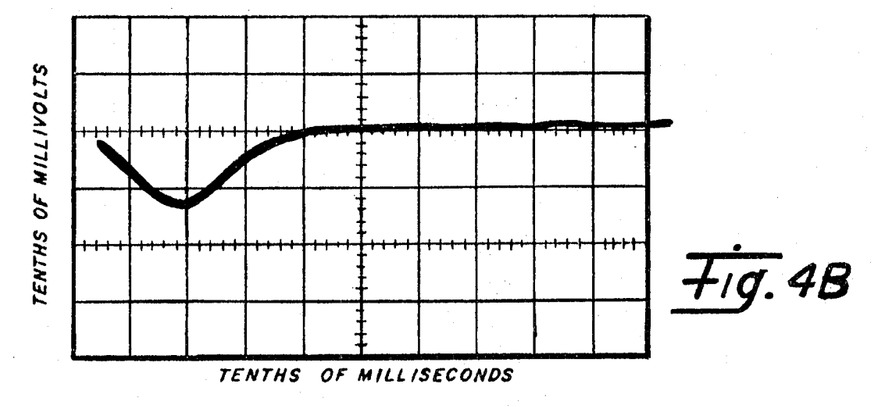
Figure 4C:
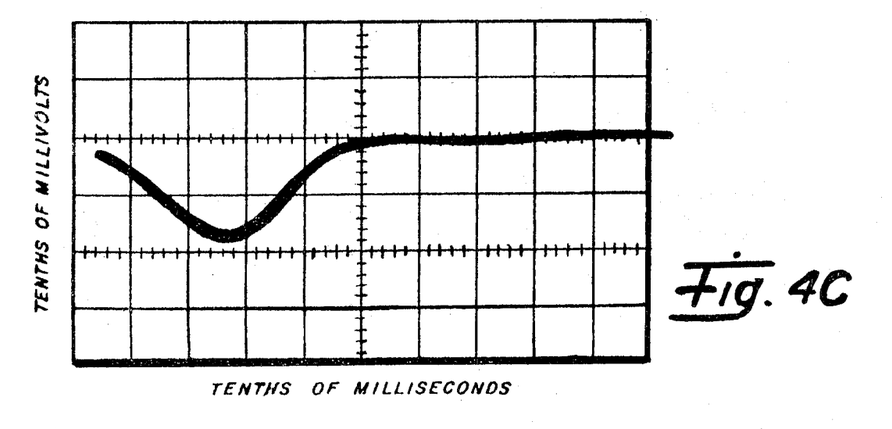

Stated more succinctly, a DC electric field is established across port 30 so that the cells (lymphocytes) are exposed to an intense electric field gradiant as they transverse port 30 (approximately $10^5$ V/m in milliseconds). This causes a voltage transient or spike in the electric field. Three typical voltage pulses are shown in FIGS. 4A, 4B and 4C of the drawing. The Y axis is calibrated in tenths of millivolts, while the X axis is in tenths of milliseconds. The voltage pulses are (1) monitored by oscilloscope 52 and frequency counter 54 to ensure that proper cell exposure and flow rate (approximately 2000 cells per second) are maintained, (2) amplified and (3) stored in multi-channel pulse-analyzer 50. Consequently, a frequency histogram can be constructed based on peak-pulse height. Control of the electric field is by the variable voltage source/amplifier 36. The variable voltage source permits a wide range of electric field strengths to be generated across port 30.

OPERATION AND METHOD OF THE INVENTION

Determination of cell membrane dielectric breakdown begins by drawing a vacuum through vacuum source 28 so as to continually flow the electrolyte or saline solution 14 through the electric field exposure tube 22. Suitable lymphocyte cells are inserted in tube-like storage container 40 and by means of the syringe-like function thereof, pressing plunger 42 causes the flow of cells from nozzle 44. These cells are drawn into port 30 and as each cell moves therethrough it acts as a resistance. The variable voltage source/amplifier 36 is set to stop at intervals of, for example, between 0 and 100 volts as the lymphocytes are drawn through the exposure tube port 30. The frequency histogram is acquired at each voltage exposure and stored. In this manner an average voltage pulse height caused by the change in resistance as each cell passes through the electric field can be recorded.

Figure 5:
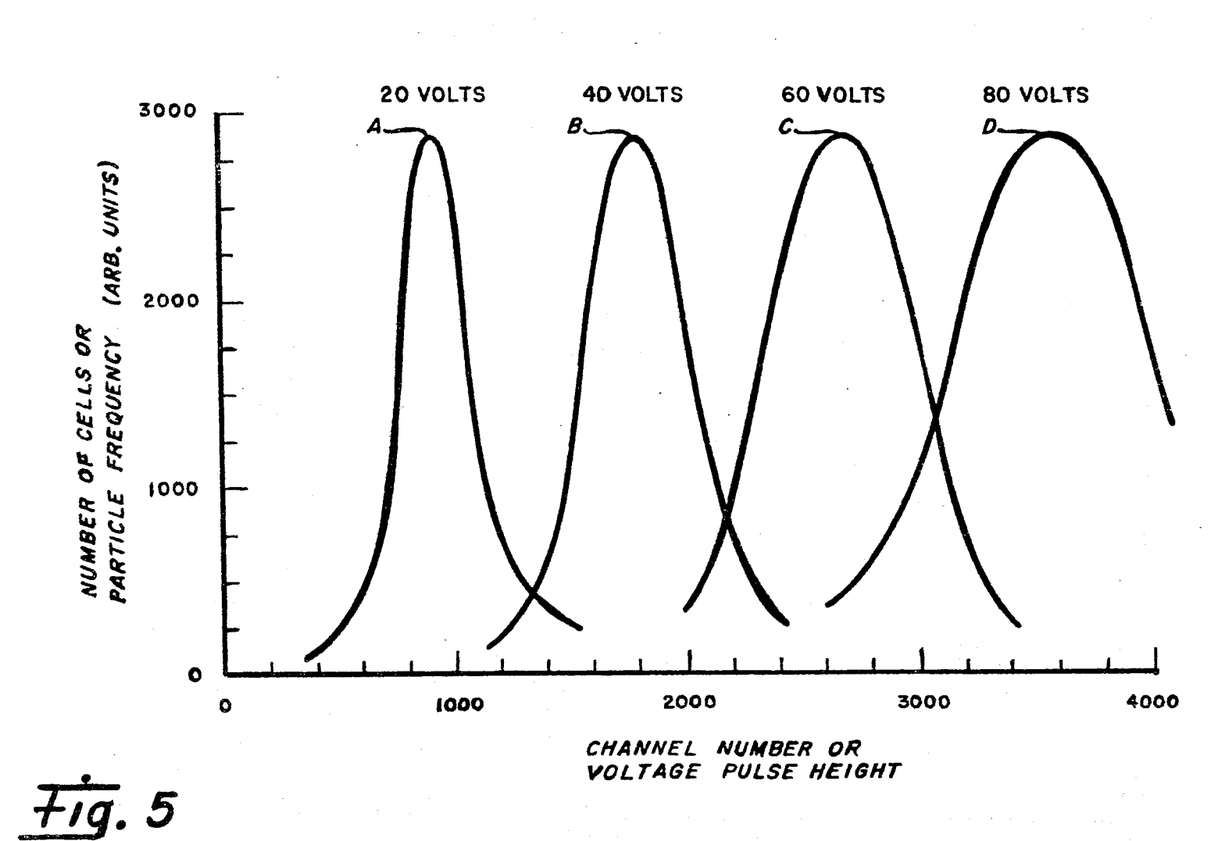
FIG. 5 illustrates a series of frequency histograms for 20-80 volts obtained using conventional polystyrene divinyl benzene spheres with the dielectric breakdown apparatus.
Figure 6:
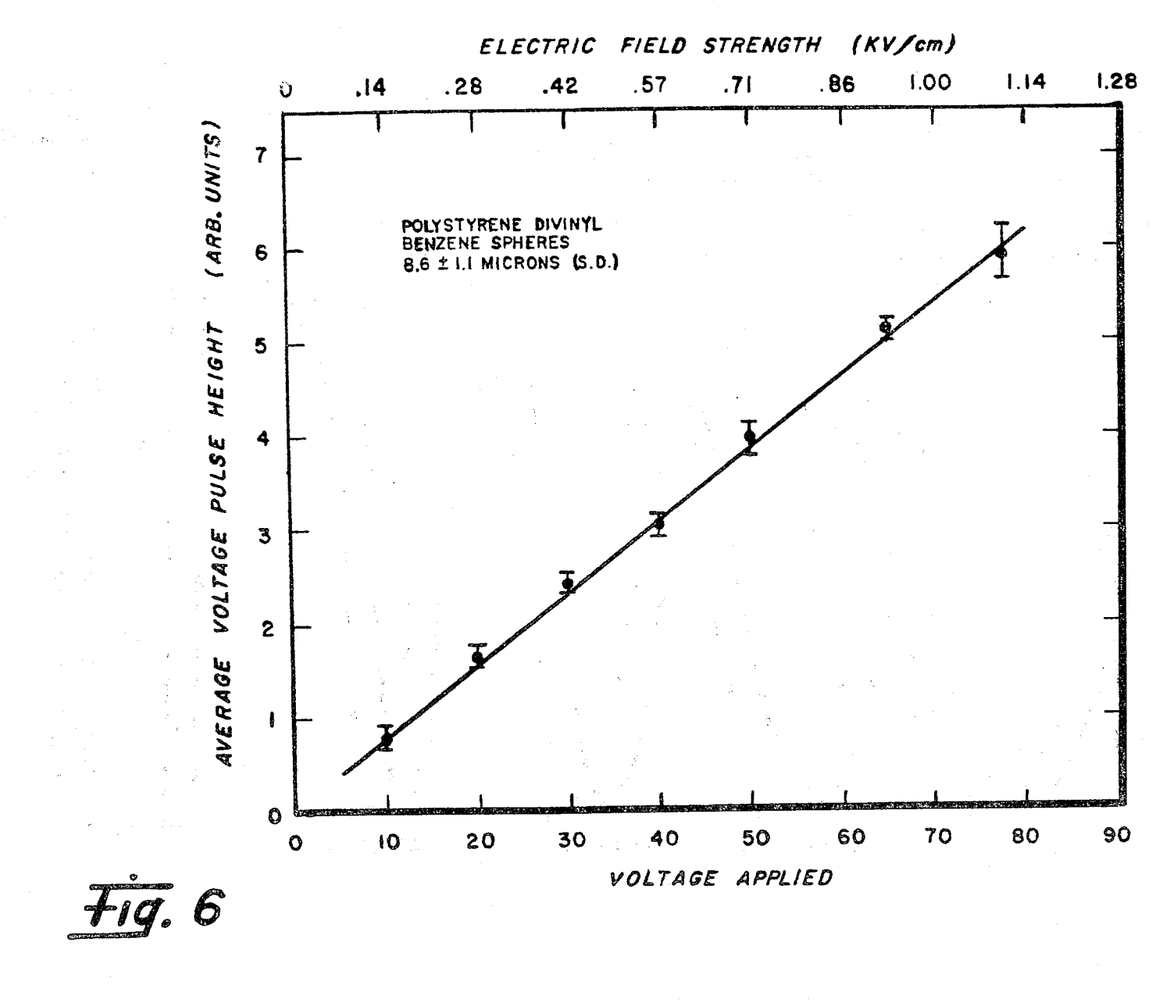
FIG. 6 is a graphic representation of the breakdown profile for polystyrene divinyl benzene spheres obtained with the dielectric breakdown apparatus.

Therefore, a breakpoint or breakdown profile can be generated. For example, FIG. 5 illustrates a series of frequency histograms for 20–80 volts obtained using conventional polystyrene divinyl benzene spheres (8.6±1.1 microns) in place of cells. Points A, B, C and D illustrate the average voltage pulse height caused by the change in resistance as each sphere (cell) passes through the electric field. The Y axis is the number of cells or particle frequency and the X axis is the channel number in the multi-channel pulse-height analyzer 50 which corresponds to increasing pulse height. As can be seen in FIG. 5 of the drawing, an average voltage pulse height, A, B, C and D, is associated with each different applied voltage. The average voltage pulse height can be plotted against applied voltage to obtain a breakpoint apparent in the dielectric breakdown profile. FIG. 6 of the drawing illustrates in graphic form the breakdown profile for the polystyrene divinyl benzene spheres. It should be noted that the line is perfectly straight or linear indicating no change in the electrical resistance of the styrene spheres over an applied electric field strength of 0.14–1.28 kilovolts per centimeter. This is expected since the spheres act as perfect dielectrics. In this way apparatus 10 can be calibrated for different size particles (1.5–20 microns) to ensure linearity of response.

Figure 7:
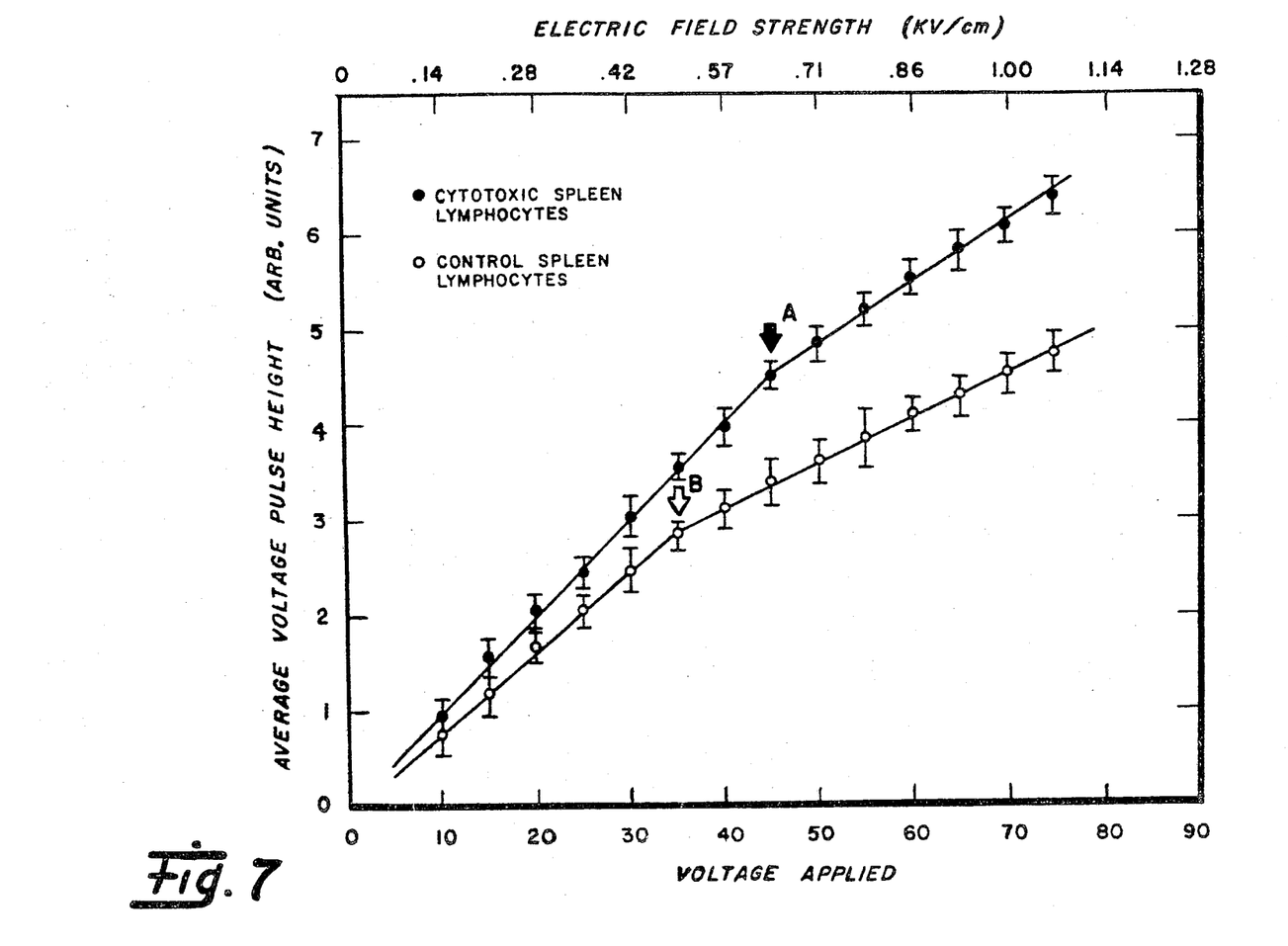
FIG. 7 is a graphic representation of the breakdown profiles for control and cytotoxic spleen lymphocytes obtained with the dielectric breakdown apparatus.

To perform the actual method for determining cell membrane dielectric breakdown of this invention on, for example, lymphocytes, the same procedure is set forth as above except that lymphocytes are substituted for the perfect dielectric polystyrene divinyl benzene spheres. As illustrated in FIG. 7 of the drawing typical lymphocyte breakdown profiles are shown. Live lymphocytes display a distinct breakdown point or change in slope in their linear profile indicated by the arrows A and B in FIG. 7. The voltage at which this occurs is the breakdown or breakpoint voltage and it indicates that the lymphocyte cell membrane has undergone dielectric collapse and cell electrical resistivity has been markedly reduced giving rise to the characteristic breakdown or breakpoint profile. It should be further noted (although not illustrated) that dead lymphocytes display a linear profile with zero slope after the breakpoint or breakdown is reached.

Since as illustrated in FIG. 7 of the drawing breakdown occurs at different points in different lymphocytes or cells a study was pursued in which control spleen lymphocytes (that is, normal cells) were subjected to the method of this invention. Such analysis yielded the breakdown point B set forth in FIG. 7 of the drawing. Thereafter cytotoxic lymphocytes were subjected to the method of this invention and resulted in the linear breakdown point A shown in FIG. 7 of the drawing.

Further investigation established that the cytotoxicity of the lymphocyte cells depended upon the degree of membrane rigidity or non-fluidity, and an elevated intrinsic membrane potential. Membrane fluidity is reflected by relative cholesterol/phospholipid composition. Thus, plasma membrane fractions of cytotoxic and non-cytotoxic lymphocytes were isolated and assayed for cholesterol and phospholipid molar ratios according to standard procedures. Table I, set forth hereinbelow, presents the cholesterol and phospholipid mole ratios for cytotoxic and non-cytotoxic cell-membrane fractions.

TABLE I

| FRACTION | PROTEIN (mg/10⁸ cells) | CHOLESTEROL (C) (ug/g protein) | PHOSPHOLIPID (P) (ug/g protein) | C/P MOLAR RATIO |
| --- | --- | --- | --- | --- |
| Cytotoxic Lymphocytes | | | | |
| Cytosol | 2.01 ± 0.06[b] | 43.32 ± 1.69 | 17.91 ± 1.74 | 2.42 ± 0.31 |
| Plasma Membrane | | 53.79 ± 1.48 | 16.42 ± 0.68 | 3.28 ± 0.62 |
| Non-cytotoxic Lymphocytes | | | | |
| Cytosol | 2.06 ± 0.04 | 48.31 ± 1.61 | 26.70 ± 0.92 | 1.81 ± 0.41 |
| Plasma Membrane | | 50.63 ± 2.14 | 24.27 ± 1.01 | 2.09 ± 0.37 |

[a]Cytosol is the crude starting material for plasma membrane; lymphocytes are homogenized and then clarified at 13,500 XG to remove nuclei, mitochondria, and lysosomes.
[b]Data expressed as mean values ± S.E. (N = 12).

Cytotoxic cell-membranes possessed a significant increase in their cholesterol/phospholipid mole ratio indicating that cytotoxic lymphocyte membranes are relatively more rigid and less fluid. This data taken together with the cytotoxicity data set forth in Table II, hereinbelow, verifies that the dielectric breakdown technique of this invention is a successful methodology for identifying lymphocytes that are tumor cell cytotoxic and that possess decreased cell membrane fluidity.

TABLE II

| LYMPHOCYTE-MEDIATED CYTOTOXICITY | | |
| --- | --- | --- |
| EFFECTOR/TARGET CELL | Cr⁵¹ RELEASED (CPM ± S.D., N = 15) | CYTO-TOXICITY INDEX |
| Cytotoxic Lymphocytes/ Cr⁵¹ EL-4 (50:1) | 43210 ± 325 | 46.8% |
| Normal Lymphocytes/ Cr⁵¹ El-4 (50:1) | 10010 ± 105 | 0.49% |
| EL-4CR⁵¹ EL-4 (Background) | 9654 ± 125 | |
| Freeze-Thawed Cr⁵¹ EL-4 (Maximal Release) | 81331 ± 371 | |

*Lymphocyte-Mediated Cytotoxicity Index
$= \frac{\text{Test} - \text{Backround}}{\text{Maximal} - \text{Backround}} \times 100$ In fact, the table set forth hereinabove suggests that lack of membrane fluidity may play a significant causative role in establishing the characteristic cell-membrane breakpoint or breakdown profiles.

TEST RESULTS OBTAINED BY THE METHOD OF THIS INVENTION

Specific application of this invention has been carried out for functionally active lymphocytes and results indicate that the method of this invention provides an accurate procedure for identifying lymphocytes that are tumor-cell cytotoxic. In such tests Balb/c (H2-d) mice were inoculated with EL-4(H2-b) lymphoma tumor cells to produce cytotoxic lymphocytes against the EL-4 tumor cells. Cytotoxic lymphocytes and normal control lymphocytes were then collected and subjected to the methodology of this invention as described hereinabove. FIG. 7 of the drawing presents breakdown profiles for normal and for cytotoxic lymphocytes. The breakdown point voltage for cytotoxic lymphocytes (solid arrow) is significantly greater than that for normal lymphocytes (open arrow).

As corroboration, cytotoxicity of these lymphocytes were experimentally determined by the standard four-hour chromium-51 radioisotope release assay. Table II presents these results and the data indicate that cytotoxic lymphocytes were 46.8% cytotoxic for the EL-4 lymphoma tumor cell compared to 0.49% for control non-cytotoxic lymphocytes. The above data indicates that the procedure of this invention can successfully distinguish between a cytotoxic lymphocyte population and non-functional control lymphocytes.

Although the description herein is mainly directed toward the utilization of lymphocyte cells and the quantification of both lymphocyte tumor-cell cytotoxicity and lymphocyte cell membrane fluidity it is believed that other abnormal or tumor cells can be detected in human or other mammals by the apparatus and method of the invention disclosed above.

For example, the cell membrane is responsible for cellular resistance in a static electric field, that is, the cell membrane acts as a perfect insulating surface under these conditions. It therefore follows that alterations or changes in the chemical composition of the cell membrane which lead to changes in cell resistivity will necessarily make such altered cells detectable in the apparatus 10 and method of this invention described hereinabove. Since an increase in cholesterol to phospholipid mole ratio is corrrelated to an increase in cell membrane breakdown point voltage, cells processing altered cholesterol and/or phospholipid are expected to exhibit increased breakdown voltages in the apparatus 10 and with the method of this invention disclosed above. This, in fact, has been demonstrated for the case of cytotoxic, $T_c$ lymphocytes, and the supporting data shown in Table II and FIG. 7. As shown in Table II cytotoxic lymphocytes posses an elevated plasma membrane cholesterol/phospholipid mole ratio compared to that for noncytotoxic lymphocytes ($3.28 \pm 0.62$ vs. $2.09 \pm 0.37$). And as expected the cytotoxic lymphocytes also posses an elevated breakdown voltage compared to noncytotoxic cells (45 vs. 35 volts) as indicated in FIG. 7. This specific example serves to illustrate the general applicability and utility of this invention in detecting cell population possessing altered membrane resistivity.

Based on the above facts and analysis it is asserted that other cell types which have undergone a transformation to alter membrane resistivity, e.g., by changing cholesterol content and hence membrane fluidity, will exhibit altered breakdown voltages. Tumor cells are one cell type reported in the scientific literature to be characterized by pathologic and dramatic changes in membrane composition. Tumor cell membranes experience a marked decrease in their cholesterol/phospholipid mole ratio and hence a significant increase in membrane fluidity. As a consequence of this change in membrane cholesterol content tumor cells will be recognizeable and distinguished from the untransformed or unaltered non-tumor cell by the method of this invention.

I claim:

1. A method for determining cell membrane dielectric breakdown comprising the steps of:
   (a) continuously passing a multitude of cells through a DC electric field,
   (b) establishing said DC electric field at a plurality of different preselected voltages,
   (c) subjecting individual cells of said multitude of cells in successive steps to said electric field at said plurality of different preselected voltages causing a relative change in resistance as each of said cells of said multitude of cells pass through said electric field,
   (d) establishing a histogram for each of said multitude of cells at each of said preselected voltages in order to define an average voltage change at each of said preselected voltages, said average voltage change being caused by said change in resistance as said cells of each of said multitude of cells pass through said electric field, and
   (e) comparing said average voltage change at each of said preselected voltages in order to determine the point at which cell membrane dielectric breakdown occurs.

2. A method of determining cell membrane dielectric breakdown as defined in claim 1 comprising the following steps of:
   (a) plotting each of said average voltage changes versus each of said preselected voltages, respectively, and
   (b) determining the point at which said plot changes its slope, said point being representative of the occurrence of said cell membrane dielectric breakdown.

* * * * *